United States Patent [19]

Bex et al.

[11] 4,217,665
[45] Aug. 19, 1980

[54] PROSTHESIS FOR USE IN VALVULOPLASTY

[75] Inventors: Jean Pierre Bex, Paris; Claude Mantel, Limours, both of France

[73] Assignee: Societe d'Utilisation Scientifique et Industrielle du Froid - Usifroid, Boulogne-Billancourt, France

[21] Appl. No.: 698,775

[22] Filed: Jun. 22, 1976

[30] Foreign Application Priority Data

Jun. 23, 1975 [FR] France .............................. 75 19506

[51] Int. Cl.³ .......................... A61F 1/22; A61B 17/00
[52] U.S. Cl. .................................. 3/1.5; 128/303 R; 128/334 R; 264/257
[58] Field of Search ..................... 3/1.5, 1; 128/334 R

[56] References Cited

U.S. PATENT DOCUMENTS

| 3,197,788 | 8/1965 | Segger | 3/1.5 |
| 3,656,185 | 4/1972 | Carpentier | 3/1.5 |
| 3,829,903 | 8/1974 | Stati et al. | 3/1 |
| 3,861,416 | 1/1975 | Wichterle | 3/1.5 X |

*Primary Examiner*—Ronald L. Frinks
*Attorney, Agent, or Firm*—Browdy and Neimark

[57] ABSTRACT

A prosthesis for use in valvuloplasty. The prosthesis is formed as a linear reducer made of a material which is compatible with implantation and which in its direction of length is incompressible and inextensible but in the direction of its width is sufficiently flexible to assume a radius of curvature identical with that of the valvules; which can have needles introduced into it without tearing; which cannot be torn by the traction effect of the suture threads and of which the reduction ratio is governed by the distension of the deficient valvule. The prosthesis is intended for the surgical correction of certain mitral or tricuspid valvular disorders.

11 Claims, 5 Drawing Figures

U.S. Patent     Aug. 19, 1980     4,217,665
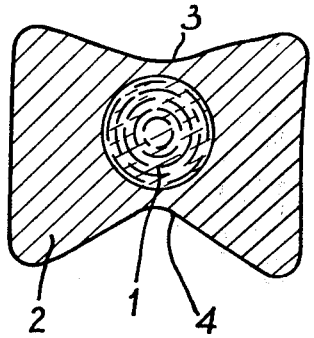
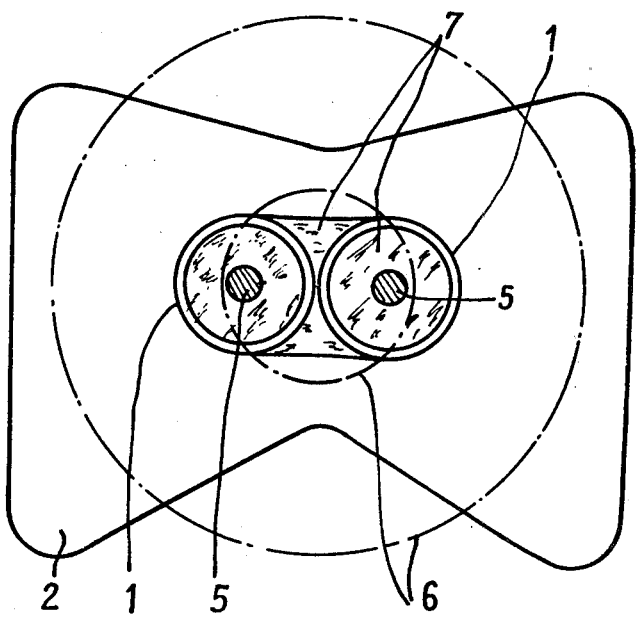
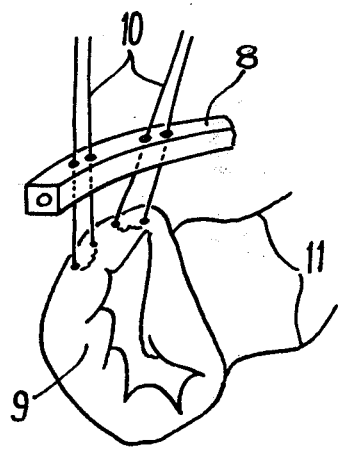
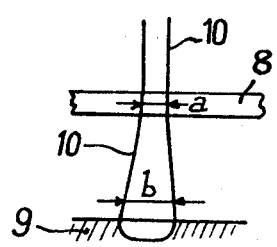
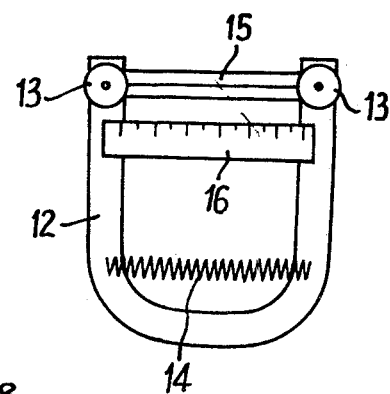

PROSTHESIS FOR USE IN VALVULOPLASTY

BACKGROUND OF THE INVENTION

This invention relates to a prosthesis for use in the surgical correction of certain mitral or tricuspid valvular disorders.

In cases of valvular insufficiency, it is common practice to retain the natural valves of a valvule and to correct the deficiencies in it. There are at present various surgical correction techniques and, in particular, the annular prostheses developed by Dr. Alain Carpentier described in French Pat. No. 69.024.41 and its first Certificate of Addition No. 69.441.24. However, these annular prosthese have certain disadvantages: they are rigid and flat whereas the valvules often have an awkward shape; their application to the initial ring may not be perfect; and they have to be sewn over their entire periphery which is an extremely delicate operation, especially in the vicinity of the His bundle. In addition, experience in functional mitral or tricuspid valvuler deficiencies has shown that the septal valve is rarely affected and that its length may be used as a base for determining the length which the other two valves ought normally to have. In fact the surgical correction comprises restoring the distended perimeter of the valves to the theoretical perimeter.

It is an object of the present invention to provide a prosthesis for mitral and tricuspid valvuloplasty which has advantages over the known prostheses both at the level of supplying surgical blocks and from the operational and post-operational levels.

SUMMARY OF THE INVENTION

According to one aspect of the present invention there is provided a prosthesis for use in valvuloplasty comprising a linear reducer made of a material which is compatible with the implantation, which in the direction of its length is incompressible and inextensible but in the direction of its width is sufficiently flexible to assume a radius of curvature identical with that of the valvules, which can have needles introduced into it without tearing, which cannot be torn by the traction effect of suture threads, and of which the reduction ratio is governed by the distension of the deficient valvule.

The texture of the linear reducer may vary, it being possible to use any elastomer which satisfies the requirements noted above for a recognized implantable material which is tolerated by the organism, such as a silicone elastomer surrounding a textile core. The textile core may have a circular cross-section and may be formed by a synthetic textile, such as a polyester or a polyamide, more especially braided nylon.

The flexible linear reducer may comprise a radio-opaque screen to enable the operation of the valve to be observed. In this case, the textile core is treated with a radio-opaque product. It may also be reinforced by a thin metal wire of, for example, silver or stainless steel.

The core of the reducer may be double both from the textile and from the metallic point of view.

The linear reducer is a narrow band with a defined length adapted to each case, a width of approximately 2 to 3 millimeters, a thickness of approximately 1 to 2 millimeters and a variable and adapted cross-section. The cross-section may be non-circular, e.g. rectangular, oval or trapezoidal, optionally curved, with grooves in the upper and lower parts of the width.

The flexible linear reducer may be provided with references spaced at regular intervals for the suture stitches and with a lower groove of such dimensions that it is able to accommodate some of the puckered tissues and an upper groove partly accommodating the extra thickness of the knots of the suture threads.

The principle of reducing the distended perimeter of valves with the flexible linear reducer according to the invention is as follows: a series of U-shaped stitches made with suitable suture thread is passed around the valve and also around that part which it is desired to reduce. These U-stitches have a certain spacing and pass through the linear reducer with a narrower spacing. When the reducer is tied onto the valve, the perimeter of the valve is thus tightened.

In mitral valvuloplasty, reduction affects only that part of the ring which is opposite the small valve. Two reference stitches which form the commisures are introduced. 8 to 10 U-stitches are introduced into the valvular ring along the small valve. Each of these stitches then transfixes the reducer-the spacing of the two sides of the "U" stitches defining the reduction ratio a/b, a being the spacing on the reducer and b the spacing on the valve. The stitches are then tied which applies the reducer to the mitral ring and reduces its perimeter in the position opposite the small valve.

In tricuspid valvuloplasty, that part of the ring opposite the septal valve is free of any prosthetic material. In that case, reduction is carried out on the front, lower portion of the ring.

Positioning of the linear reducer according to the invention is facilitated by using a U-shaped presenter on which the reducer band is placed at the front and of which the rear part comprises a slightly extended spring which acts as a rack or comb for separating the suture threads extending through the reducer before its application to the valvule.

Some of the numerous advantages of the linear reducer according to the invention will have been deduced from the foregoing. The supplying of surgical blocks and a high degree of flexibility, because the profile of adapted length enables the specialist surgeon to work with profiles having the length required for each operation, whereas other known prostheses are rigid and fixed in their dimensions.

The flexible reducer according to the invention has the advantage that it can be positioned more rapidly because the number of fixing points is reduced by one third in relation to other known valvuloplasty techniques. In addition, there is a reduction in the danger of lesions of the His bundle, the aortic valve and the circumflex artery in the zone which is incapable of withstanding suture stitches. On the other hand, the specialist surgeon has the opportunity to adapt the reduction ratio as required in dependence upon the distension of the affected ring or in dependence upon the age of the patient.

At the post-operational level, the flexible linear reducer eliminates the danger of deficiencies in conduction by compression of the His bundle in the case of mitral and tricuspid valvuloplasty, and maintains the flexibility of the auriculoventricular ring, thereby ensuring better continence.

DESCRIPTION OF EMBODIMENTS

For a better understanding of the invention, and to show more clearly how the same may be carried into effect, reference will now be made, by way of example, to the accompanying drawings in which:

FIG. 1 is a cross-sectionaL view of one embodiment of a prosthesis in accordance with the invention;

FIG. 2 is a cross-sectional view of another embodiment of a prosthesis in accordance with the invention;

FIGS. 3 and 4 are two views showing the implantation of a prosthesis; and

FIG. 5 shows a device for use in implanting a prosthesis.

Referring to the drawing, FIG. 1 is a view in section of one possible profile of the reducer. A core of braided nylon, optionally with a radio-opaque wire, is denoted by the reference (1), the reducer itself is made of a silicone elastomer and is denoted by the reference (2), and the upper and lower grooves are denoted by the references (3) and (4), respectively, the lower groove being approximately twice as deep as the upper groove.

In FIG. 2 there is a view in section of the profile of the reducer when it surrounds a double core. The reducer itself is denoted by the reference (2), the textile core is denoted by the reference (1) and the metal core by the reference (5). The initial tube of a silicone elastomer is denoted by the reference (6) and the silicone elastomer filling by the reference (7).

FIGS. 3 and 4 illustrate the implantation of a reducer (8) in a valve (9) by means of suture threads (10) on the reducer and the valve, the reference threads (11) and the reduction ratio a/b.

FIG. 5 is a plan view of a U-shaped presenter (12) which is provided with tightening screws (13) and a slightly extended spring (14) around which the U-threads of the prosthesis are guided. The reducer (15) is held by the screws (13), and a small graduated rule (16) may optionally be arranged between the arms of the U.

The physical characteristics which the linear reducer is required to show necessitate a particular method of production.

The outer cover of the reducer which is made of a silicone elastomer is a tube obtained by extrusion and only prevulcanized to retain its shape. The cross-section of the initial tube in square millimeters is substantially the cross-section of the profile which it is desired to obtain, taking into account the reinforced textile core which will be included therein. The prevulcanized tube is provided with its textile core and then calibrated to a diameter corresponding to the cross-section of the finished profile. The whole is then shaped in a mold and vulcanized.

The shaping operation and final vulcanization stage are carried out at the same time under heat in a mold, the pressure being mechanically regulated by the characteristics of the material, the cross-section of the closed mold having to correspond to the cross-section of the tube reinforced with its silicone-impregnated core.

It has been found to be of advantage initially to position the tube in the mold in order to hold the prevulcanized tube by the frictioal forces on the walls, thus enabling the silicon-coated textile core to be introduced without deforming the prevulcanized tube.

One example of production illustrating the mode of operation is given in the following.

The mold is designed for a profile length of 200 mm. The tube (measuring 2.3×0.8) is extruded from a silicone elastomer in a screw extruder at ambient temperature. The tube is then prevulcanized by treatment in an oven for 15 minutes at 160° C. The tube is then adjusted to a length of 200 millimeters plus the gripping or holding length. It is then introduced into the closing mold for the first time in the absence of pressure and at ambient temperature. A length of 4/10 mm stainless steel wire is then introduced at the center of the tube.

At the same time, the textile sleeve or core is prepared, initially in a length of approximately 400 mm. The wire core of braided polyester is then replaced by a core of 15/100 mm stainless steel wire with impregnation of the metallic wire with silicone elastomer in solution in acetic acid. After shaping into a pin-like structure with a length of 200 mm, the pin itself is impregnated with silicone and the 4/10 mm wire is attached to the textile pin.

The coated textile pin is then introduced into the tube by pulling with the wire without deforming the prevulcanized tube. After the mold has been opened, the core+tube assembly is removed and calibrated to a diameter of 2.3 mm by passage through a die, care being taken to pull the assembly. The assembly is then reintroduced into the mold, the mold is closed and the assembly molded and vulcanized in the mold heated to a temperature of approximately 160° C. for a period of about 3 hours.

We claim:

1. A prosthesis for use in valvuloplasty comprising a linear reducer made of a material which is compatible with the implantation, which in the direction of its length is incompressible and inextensible but in the direction of its width is sufficiently flexible to assume a radius of curvature identical with that of the valvules, which can have needles introduced into it without tearing, which cannot be torn by the traction effect of suture threads, and of which the reduction ratio is governed by the distension of the deficient valvule.

2. A prosthesis for valvuloplasty as claimed in claim 1, wherein the linear reducer is a profile of a silicone elastomer surrounding a textile core.

3. A prosthesis for valvuloplasty as claimed in claim 2, wherein the textile core is of a synthetic textile material.

4. A prosthesis for valvuloplasty as claimed in claim 3, wherein said synthetic textile material is a braided synthetic selected from the group consisting of polyester and polyamide.

5. A prosthesis for valvuloplasty as claimed in claim 3, wherein said textile core is treated with a radio-opaque product.

6. A prosthesis for valvuloplasty, as claimed in claim 3, wherein said textile core is reinforced by a thin metal wire.

7. A prosthesis for valvuloplasty as claimed in claim 6, wherein said thin metal wire is selected from the group consisting of silve wire and stainless steel wire.

8. A prosthesis for valvuloplasty as claimed in claim 1, wherein the linear reducer is a narrow band whose length is adapted for its intended use, whose width is in the range of from about 2 to about 3 mm, whose thickness is in the range of from about 1 to about 2 mm and whose cross-section is variable and adapted for its intended use.

9. A prosthesis for valvuloplasty as claimed in claim 8 wherein the cross-section is non-circular, and optionally is recessed in groove-like form on the lower and upper parts of the width.

10. A prosthesis for valvuloplasty as claimed in claim 1, wherein it is provided with references spaced at regular intervals for the suture stitches and with a lower groove of such dimensions that it is able to accommodate some of the puckered tissues and an upper groove partly accommodating the extra thickness of the knots of the suture threads, the lower groove being deeper than the upper groove.

11. A prosthesis for valvuloplasty as claimed in claim 2, wherein the textile core of the reducer is double.

* * * * *